United States Patent [19]

Devon et al.

[11] Patent Number: 5,344,988
[45] Date of Patent: Sep. 6, 1994

[54] HYDROFORMYLATION PROCESS USING NOVEL PHOSPHINE-RHODIUM CATALYST SYSTEM

[75] Inventors: Thomas J. Devon; Gerald W. Phillips; Thomas A. Puckette; Jerome L. Stavinoha; Jeffrey J. Vanderbilt, all of Longview, Tex.

[73] Assignee: Eastman Chemical Company, Kingsport, Tenn.

[21] Appl. No.: 200,023

[22] Filed: Feb. 22, 1994

Related U.S. Application Data

[62] Division of Ser. No. 69,478, Jun. 1, 1993, abandoned.

[51] Int. Cl.⁵ .............................................. C07C 45/50
[52] U.S. Cl. ...................... 568/454; 556/21; 568/451
[58] Field of Search ................. 556/21; 568/451, 454

[56] References Cited

U.S. PATENT DOCUMENTS

| | | | |
|---|---|---|---|
| 4,139,565 | 2/1979 | Unruh et al. | 568/454 |
| 4,152,344 | 5/1979 | Unruh et al. | 568/454 |
| 4,215,077 | 7/1980 | Matsumoto et al. | 568/454 |
| 4,247,486 | 1/1981 | Brewester et al. | 568/454 |
| 4,694,109 | 9/1987 | Devon et al. | 568/454 |
| 4,760,194 | 7/1988 | Phillips et al. | 568/454 |
| 4,851,585 | 7/1989 | Barner et al. | 568/454 |
| 4,960,949 | 10/1990 | Devon et al. | 568/454 |

Primary Examiner—Werren B. Lone
Attorney, Agent, or Firm—J. Frederick Thomsen

[57] ABSTRACT

Disclosed are bis-phosphine compounds having the general formula

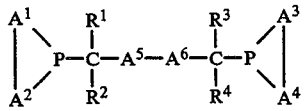

wherein:
each of $A^1$, $A^2$, $A^3$ and $A^4$ is an arylene radical wherein (i) each phosphorus atom P is bonded to a ring carbon atom of $A^1$ and $A^2$ and to a ring carbon atom of $A^3$ and $A^4$, (ii) $A^1$ and $A^2$, and $A^3$ and $A^4$ are bonded to each other by ring carbon atoms and (iii) each of the residues

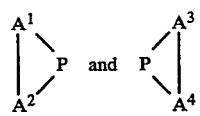

constitutes a 5-membered ring;
each of $A^5$ and $A^6$ is an arylene radical wherein $A^5$ and $A^6$ are bonded to each other and to residues $R^1$—C—$R^2$ and $R^3$—C—$R^4$ by ring carbon atoms and $R^1$—C—$R^2$ and $R^3$—C—$R^4$ are connected to each other through a chain of 4 carbon atoms; and $R^1$, $R^2$, $R^3$ and $R^4$ each represents hydrogen or a hydrocarbyl radical containing up to about 8 carbon atoms. Also disclosed are catalyst systems comprising one or more of the above phosphine compounds and rhodium, catalyst solutions comprising one or more the above phosphine compounds, rhodium and a hydroformylation solvent, and hydroformylation processes wherein olefins are contacted with carbon monoxide, hydrogen and the catalyst solution to produce aldehydes.

7 Claims, No Drawings

HYDROFORMYLATION PROCESS USING NOVEL PHOSPHINE-RHODIUM CATALYST SYSTEM

This is a divisional application of copending application Ser. No. 07/069,478 filed Jun. 1, 1993, abandoned.

This invention pertains to certain novel bis-phosphine ligand compounds, to novel hydroformylation catalyst systems containing the phosphine ligands and the use of the catalyst system in the hydroformylation of various α-olefins to produce aldehydes. The catalyst system produces aldehydes having a high ratio of normal (straight-chain) to iso (branched-chain) aldehydes in good to excellent rates.

The hydroformylation reaction is useful in the preparation of aldehyde products by the reaction of one mole of olefin with one mole each of hydrogen and carbon monoxide. The reaction is especially useful in the preparation of normal and iso-butyraldehyde from propylene. These materials in turn are converted into many chemical products such as n-butanol, 2-ethyl-hexanol, n-butyric acid, iso-butanol, neopentyl glycol and the like. The hydroformylation of higher α-olefins such as 1-octene, 1-hexene and 1-decene yield aldehyde products which are useful feedstocks for the preparation of detergent alcohols. It is known that linear (normal) carbon-chain alcohol products are particularly desirable for use in detergent grade products. According to U.S. Pat. No. 4,215,077, allyl alcohol is hydroformylated to produce an intermediate which may be converted to 1,4-butanediol. Again, in this use of the hydroformylation reaction it is desirable to obtain aldehyde products where the formyl group is added to the terminal position of the olefin thus obtaining linear carbon-chain aldehyde products.

The original hydroformylation catalyst systems were based on cobalt carbonyl catalysts and required high operating reactor pressures and temperatures in order to obtain practical aldehyde production rates. See, for example, J. Falbe, Carbon Monoxide in Organic Synthesis, pp. 3–75, Springer-Verlag, Berlin 1970. A consequence of these required operating conditions was the sacrifice of much olefin feedstock to alkane formation and the conversion of some of the desired aldehyde products to a complex mixture of high-boiling aldol condensation products. Such by-product formation represents a severe monetary loss in terms of wasted olefin feedstock and the expense of processing the high-boiling by-products to partially convert them into useful products and/or the environmental costs associated with their disposal. Additionally, the cobalt carbonyl catalyst systems are not particularly selective for preparing linear aldehyde products. For example, in the hydroformylation of propylene, the practical normal to branched product ratio varies from about 1.7:1 up to 2.2:1 depending on the reactor conditions.

The many disadvantages of cobalt-catalyzed hydroformylation processes led to the development of catalyst systems comprising the transition metal rhodium and organophosphorus compounds, referred to as ligands, which stabilize the active catalyst at low reactor pressures. An early patent, U.S. Pat. No. 3,168,553, discloses that catalyst systems consisting of rhodium and certain trialkylphosphine ligands such as tri-n-butylphosphine could be used to hydroformylate α-olefins at reactor pressures of 28.5 to 56.2 bars absolute (about 400–800 pounds per square inch gauge; psig) at 195° C. However, the disclosed catalyst systems produced significant amounts of alkane and alcohol by-products the high temperatures used, but they did represent an advance in technology by lowering reactor pressure and by increasing the linear to branched product ratios compared to cobalt-based catalyst systems.

A further improvement in rhodium-based hydroformylation catalyst systems was the use of rhodium in combination with triarylphosphine ligands such as triphenylphosphine. This catalyst system is described in U.S. Pat. No. 3,527,809 and is used commercially in hydroformylation plants to manufacture much of the n-butyraldehyde-derived products made in the world today. U.S. Pat. No. 4,247,486 reports that hydroformylation processes utilizing this catalyst system typically operate at a reactor pressure of 21.7 bars absolute (about 300 psig) at 95° C. and produce butyraldehdye product consisting of a normal:iso ratio of about 10:1. The '486 patent discloses that the best results are obtained when a high triphenylphosphine:rhodium mole ratio is maintained in the reactor and the carbon monoxide partial pressure is kept below 2.4 bars absolute (about 35 pounds per square inch absolute; psia).

While the catalyst system disclosed in U.S. Pat. Nos. 3,527,809 and 4,247,486 represented a significant advance in hydroformylation technology, the system has some undesired aspects. "Intrinsic" catalyst deactivation has been a notable problem and several patents relating to this and the associated recovery rhodium from catalyst residues have issued. See, for example, U.S. Pat. Nos. 4,277,627, 4,283,304, 4,283,562 and 4,292,448. Furthermore, the large amount of triphenylphosphine ligand required represents a significant inventory cost for the catalyst system. Therefore, efforts have been directed towards the development of low pressure, rhodium-based hydroformylation catalysts that require low concentrations of organophosphine ligand in the catalyst solution and produce linear aldehyde products in a high yield. The use of 1,1'-bis(diphenylphosphino)ferrocene as the ligand component of a catalyst system in the hydroformylation of α-olefins is described in U.S. Pat. Nos. 4,138,420 and 4,152,344).

Catalyst systems comprising rhodium and trans-1,2-bis(diphenylphosphinomethyl)cyclobutane as well as other trans-1,2-bis(diphenylphosphinomethyl)cycloalkanes are described in U.S. Pat. No. 4,139,565. U.S. Pat. No. 4,201,728 discloses the use of bidentate ligands such as 1,1'-bis(diphenylphosphino)ferrocene and the cycloalkane bidentate ligands of U.S. Pat. No. 4,139,565 in combination with monodentate ligands such as triphenylphosphine and triisobutylphosphine in monodentate ligand:rhodium mole ratios ranging from 2:1 up to 100:1 to obtain higher linear aldehyde selectivity. A similar patent, U.S. Pat. No. 4,215,077, discloses the use of catalyst systems comprising a bidentate α,ω-bis(diphenylphosphino)alkane ligand in combination with high ratios of triarylphosphine:rhodium catalyst in the hydroformylation of allyl alcohol and propylene.

The spatial arrangement of diphenylphosphino moieties in bidentate ligands has a great impact on the selectivity to linear aldehyde product and may be useful in obtaining a desired linear to branched product ratio. Thus, according to U.S. Pat. No. 4,960,949, the hydroformylation of propylene using a catalyst system comprising α,α'-bis(diphenylphosphino)-o-xylene and rhodium yields butyraldehyde product with linear to branched (N/Iso) ratios ranging from 2.4:1 up to 2.8:1. U.S. Pat. No. 4,774,362 discloses that a butyraldehyde N/Iso ratio of 4.0:1 is obtained when using a catalyst system comprising $\beta,\beta'$-1,2-bis(diphenylphosphinoethyl)-benzene and rhodium in the hydroformylation of propylene. The '362 patent also discloses that the N:Iso ratio may be increased to 5.9:1 by the use of a catalyst system comprising $\alpha,\beta'$-bis(diphenylphosphino)-o-ethyltoluene and rhodium.

U.S. Pat. Nos. 4,694,109, 4,755,624, 4,760,194, 4,851,581 and 4,904,808 disclose processes for the hydroformylation of propylene in the presence of catalyst systems comprising rhodium and certain bidentate ligands which produce butyraldehyde products having N:Iso ratios in excess of 25/1 and which, therefore, are of particular value for producing linear aldehyde products. The bidentate ligands are characterized by having two diphenylphosphinomethyl groups attached at the 2 and 2' positions of aromatic hydrocarbons having a 1,1'-biphenyl, 1,1'-binaphthyl or 1-phenylnaphthalene nucleus.

We have discovered that the hydroformylation of $\alpha$-olefin compounds in the presence of a catalyst system comprising rhodium and certain novel phosphine ligands provides aldehyde products having high N:Iso ratios. The novel phosphine compounds provided by the present invention have the general formula:

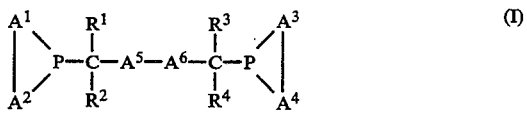 (I)

wherein:
each of $A^1$, $A^2$, $A^3$ and $A^4$ is an arylene radical, e.g., a divalent, carbocyclic aromatic group containing 6 to 10 ring carbon atoms, wherein (i) each phosphorus atom P is bonded to a ring carbon atom of $A^1$ and $A^2$ and to a ring carbon atom of $A^3$ and $A^4$, (ii) $A^1$ and $A^2$ and $A^3$ and $A^4$ are bonded to each other by ring carbon atoms and (iii) each of the residues

 (II)

and

 (III)

constitutes a 5-membered ring;

each of $A^5$ and $A^6$ is an arylene radical, e.g., a divalent, carbocyclic aromatic group containing 6 to 10 ring carbon atoms, wherein $A^5$ and $A^6$ are bonded to each other and to residues $R^1$—C—$R^2$ and $R^3$—C—$R^4$ by ring carbon atoms and $R^1$—C—$R^2$ and $R^3$—C—$R^4$ are connected to each other through a chain of 4 carbon atoms; and $R^1$, $R^2$, $R^3$ and $R^4$ each represents hydrogen or a hydrocarbyl radical containing up to about 8 carbon atoms.

The distinctive feature of the phosphine ligands of formula (I) is flat residues (II) and (III) consisting of two aromatic rings connected together at what would be considered the two ortho positions of the two halves. The nature of residues (II) and (III) is that there is coplanarity of the overlapping molecular orbitals of the two aromatic group halves with the phosphorus atom that constitutes part of the five membered ring in the center of the residues. While the reasons for the catalyst performance are not clear, residues (II) and (III) do impart to the resulting rhodium hydroformylation catalyst the ability to produce aldehyde product with high selectivity to linear product. It is also not understood if the singularity of residues (II) and (III) plays a role in this selectivity as opposed to the attachment of two separate aryl groups to the phosphorus atom "Y" as disclosed in U.S. Pat. No. 4,694,109.

The hydrocarbyl groups which each of $R^1$, $R^2$, $R^3$ and $R^4$ may represent may be alkyl, aryl substituted alkyl, cycloalkyl, alkyl substituted cycloalkyl, aryl or alkyl substituted aryl of up to about 8 carbon atoms. It is preferred that $R^1$ and $R^3$ represent hydrogen or alkyl of up to about 4 carbon atoms and $R^2$ and $R^4$ are hydrogen. Each of $R^1$, $R^2$, $R^3$ and $R^4$ most preferably is hydrogen, i.e., the residues $R^1$—C—$R^2$ and $R^3$—C—$R^4$ most preferably are methylene groups.

Examples of the arylene groups represented by each of $A^1$, $A^2$, $A^3$, $A^4$, $A^5$ and $A^6$ include the divalent radicals having the formulas:

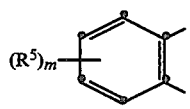 (IV)

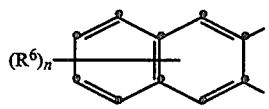 (V)

and

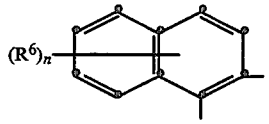 (VI)

wherein $R^5$ and $R^6$ may represent one or more substituents independently selected from alkyl, alkoxy, hydroxy, halogen, formyl, alkanoyl, aroyl, carboxyl, carboxylate salts, alkoxycarbonyl, alkanoyloxy, cyano, sulfonic acid, sulfonate salts and the like. The alkyl moiety of the aforesaid alkyl, alkoxy, alkanoyl, alkoxycarbonyl and alkanoyloxy groups typically contains up to about 8 carbon atoms. Although it is possible for m to represent 0 to 4 and for n to represent 0 to 6, the value of each of m and n usually will not exceed 2. $R^5$ and $R^6$ preferably represent lower alkyl, i.e., straight-chain and branched-chain alkyl of up to about 4 carbon atoms, and m and n each represent 0, 1 or 2.

A second embodiment of our invention is a novel catalyst system comprising one or more of the novel phosphine ligands of formula (I) and rhodium. The ligands are considered as chelating ligands such that they interact with the rhodium atom in a one to one molar stoichiometry to form the active catalyst. The catalytically active combination is believed to be a combination of one rhodium atom with one hydrogen atom, two carbon monoxide molecules and one phosphine ligand molecule. Thus, it is preferred to have a ligand:- rhodium mole ratio of at least 1:1 in the catalyst solution. Higher ligand:rhodium mole ratios are used in practice to offset problems associated with ligand oxidation that normally occur under hydroformylation of olefins with traces of oxygen in the feeds to the reactor. There is no upper limit on the ligand:rhodium mole ratio in the catalyst system, but solubility limits and economic considerations based on inventory dictate a practical upper limit, e.g., a ligand:rhodium mole ratio of up to about 100:1. There is no advantage in the use of ligand:rhodium mole ratios of less than 1:1 since such low ratios would leave some of the rhodium unstabilized for operation at the low reactor pressures which may be used in the operation of the process of the present invention. The preferred ligand:rhodium ratio is in the range of about 10:1 to 1.

Rhodium compounds that may be used as a source of rhodium for the active catalyst include rhodium II or rhodium III salts of carboxylic acids of which examples such as di-rhodium tetraacetate dihydrate, rhodium(II) isobutyrate, rhodium(II) 2-ethylhexanoate, rhodium(II) benzoate and rhodium(II) octanoate exist. Also, rhodium carbonyl species such as $Rh_4(CO)_{12}$, $Rh_6(CO)_{16}$ and rhodium(I) acetylacetonate dicarbonyl may be suitable rhodium feeds. Additionally, rhodium organophosphine complexes such as tris(triphenylphosphine) rhodium carbonyl hydride may be used when the organophosphine moieties of the complex fed are easily displaced by the phosphine ligands of the present invention. Less desirable rhodium sources are rhodium salts of strong mineral acids such as chlorides, bromides, nitrates, sulfates, phosphates and the like.

A third embodiment of our invention concerns a novel catalyst solution comprising (1) one or more of the novel phosphine ligands of formula (I), (2) rhodium and a hydroformylation solvent. This embodiment comprises a solution of the active catalyst in which a carbonylation process such as the hydroformylation of an ethylenically-unsaturated compound may be carried out.

The hydroformylation reaction solvent may be selected from a wide variety of compounds, mixture of compounds, or materials which are liquid at the pressure at which the process is being operated. Such compounds and materials include various alkanes, cycloalkanes, alkenes, cycloalkenes, carbocyclic aromatic compounds, alcohols, esters, ketones, acetals, ethers and water. Specific examples of such solvents include alkane and cycloalkanes such as dodecane, decalin, octane, iso-octane mixtures, cyclohexane, cyclooctane, cyclododecane, methylcyclohexane; aromatic hydrocarbons such as benzene, toluene, xylene isomers, tetralin, cumene, alkyl-substituted aromatic compounds such as the isomers of diisopropylbenzene, triisopropylbenzene and tert-butylbenzene; and alkenes and cycloalkenes such as 1,7-octadiene, dicyclopentadiene, 1,5-cyclooctadiene, octene-1, octene-2, 4-vinylcyclohexene, cyclohexene, 1,5,9-cyclododecatriene, 1-pentene and crude hydrocarbon mixtures such as naphtha and kerosene. The aldehyde product of the hydroformylation process also may be used. In practice, the preferred solvent is the higher boiling by-products that are naturally formed during the process of the hydroformylation reaction and the subsequent steps that are required for aldehyde product isolation. The main criteria for the solvent is that it dissolves the catalyst and olefin substrate and does not act as a poison to the catalyst.

The concentration of the rhodium and ligand in the hydroformylation solvent or reaction mixture is not critical for the successful operation of our invention. As mentioned hereinabove, a ligand:rhodium mole ratio of at least 1:1 normally is maintained in the reaction mixture. The absolute concentration of rhodium in the reaction mixture or solution may vary from 1 mg/liter up to 5000 mg/liter or more. When the process is operated within the practical conditions of this invention, the concentration of rhodium in the reaction solution normally is in the range of about 50 to 300 mg/liter. Concentrations of rhodium lower than this range generally do not yield acceptable reaction rates with most olefin reactants and/or require reactor operating temperatures that are so high as to be detrimental to catalyst stability. Higher rhodium concentrations are not preferred because of the high cost of rhodium.

The fourth embodiment of the present invention pertains to a hydroformylation process utilizing the above-described catalyst systems and solutions. The process of the present invention therefore is a process for preparing an aldehyde which comprises contacting an olefin, hydrogen and carbon monoxide with a solution of a catalyst system comprising rhodium and a phosphine ligand of formula (I) wherein the mole ratio of phosphine ligand:rhodium is at least 1:1. The olefins which may be hydroformylated by means of our novel process comprise aliphatic, including ethylenically-unsaturated, low molecular weight polymers, alicyclic, aromatic and heterocyclic mono-, di- and tri-olefins containing up to about 40 carbon atoms. Examples of the aliphatic olefins which may be utilized in the process include unsubstituted and substituted, aliphatic mono-α-olefins containing up to about 20 carbon atoms. Examples of the groups which may be present on the substituted mono-α-olefins include hydroxy; alkoxy including ethers and acetals; alkanoyloxy such as acetoxy; amino including substituted amino; carboxy; alkoxycarbonyl; carboxamido; keto; and the like. Preferred aliphatic mono-α-olefins have the general formulas:

$H_2C=CH-R^7$ and $H_2C=CH-R^8-R^9$ wherein
$R^7$ is hydrogen or straight- or branched-chain alkyl of up to about 8 carbon atoms;
$R^8$ is straight- or branched-chain alkylene of up to about 18 carbon atoms; and
$R^9$ is hydroxy, alkoxy of up to about 4 carbon atoms, alkanoyloxy of up to about 4 carbon atoms, carboxyl or alkoxycarbonyl of 2 to about 10 carbon atoms.

Specific examples of the aliphatic mono-α-olefins include ethylene, propylene, 1-butene, 1-octene, allyl alcohol and 3-acetoxy-1-propene.

The aliphatic, di-olefins may contain up to about 40 carbon atoms. Preferred aliphatic, di-olefins have the general formula:

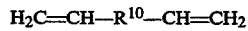

$H_2C=CH-R^{10}-CH=CH_2$ wherein $R^{10}$ is straight- or branched-chain alkylene having 1 to about 18 carbon atoms.

The cyclic olefins which may be used in the hydroformylation process of the present invention may be cycloalkenes, e.g., cyclohexene, 1,5-cyclooctadiene, and cyclodecatriene, and from various vinyl-substituted cycloalkanes, cycloalkenes, heterocyclic and aromatic compounds. Examples of such cyclic olefins include 4-vinylcyclohexene, 1,3-cyclohexadiene, 4-cyclohexene-carboxylic acid, methyl 4-cyclohexene-carboxylic acid, 1,4-cyclooctadiene and 1,5,9-cyclododecatriene. The olefin reactants which are particularly preferred comprise mono-α-olefins of 2 to 10 carbon atoms, especially propylene.

The reaction conditions used are not critical for the operation of the process and conventional hydroformylation conditions normally are used. The process requires that an olefin is contacted with hydrogen and carbon monoxide in the presence of the novel catalyst system described hereinabove. The preferred hydroformylation reaction temperatures are from 50 to 135° C. with the most favored reaction temperatures ranging from 75° to 125° C. Higher reactor temperatures are not favored because of increased rates of catalyst decomposition while lower reactor temperatures result in relatively slow reaction rates. The total reaction pressure may range from about ambient or atmospheric up to 36 bars absolute (about 500 psig). The hydrogen:carbon monoxide mole ratio in the reactor likewise may vary considerably ranging from 10:1 to 1:10 and the sum of the absolute partial pressures of hydrogen and carbon monoxide may range from 0.3 to 36 bars absolute. The carbon monoxide partial pressure in the reactor preferably is less than 4.2 bars absolute since such relatively low carbon monoxide partial pressures increase both the rate of reaction and the selectivity to the linear aldehyde isomer. Although there is no well-defined lower carbon monoxide partial pressure, a lower limit of 0.07 bar absolute carbon monoxide partial pressure is the practical lower limit since the reaction is then in a starved condition for carbon monoxide for the formation of the aldehyde product.

The amount of olefin present in the reaction mixture also is not critical. For example, relatively high-boiling olefins such as 1-octene may function both as the olefin reactant and the process solvent. In the hydroformylation of a gaseous olefin feedstock such as propylene, the partial pressures in the vapor space in the reactor typically are in the range of about 0.07 to 35 bars absolute. In practice the rate of reaction is favored by high concentrations of olefin in the reactor. In the hydroformylation of propylene, the partial pressure of propylene preferably is greater than 1.4 bars, e.g., from about 1.4 to 10 bars absolute. In the case of ethylene hydroformylation, the preferred partial pressure of ethylene in the reactor is greater than 0.14 bars absolute.

Any of the known hydroformylation reactor designs or configurations may be used in carrying out the process provided by the present invention. Thus, a gas-sparged, vapor take-off reactor design as disclosed in the examples set forth herein may be used. A reactor design where catalyst and feedstock are pumped into a reactor and allowed to overflow with product aldehyde, i.e. liquid overflow reactor design, is also suitable. A trickle-bed reactor design also is suitable for this process.

The bis-phosphine ligands of formula (I) may be prepared using reaction schemes analogous to published procedures. For example, the ligands may be prepared by the following reaction:

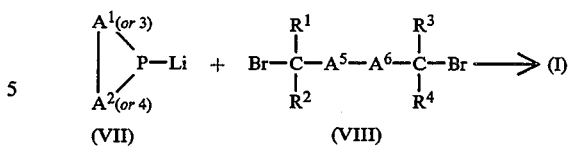

wherein $A^1$, $A^2$, $A^3$, $A^4$, $A^5$, $A^6$, $R^1$, $R^2$, $R^3$ and $R^4$ are defined hereinabove. The anionic lithio compounds of formula (VII) may be prepared by the general method described by T. Hayashi et al., Bull. Chem. Soc. Japan Vol. 52, pp. 2605–8 (1979). Thus anion (VII) is formed by the action of lithium on the intermediate having the structure:

wherein the phenyl group is selectively cleaved from the phosphorous atom thereby leaving the lithio anion of formula (VII). The intermediates of formula (IX) may be prepared using the method of N. A. Nesmeyanov et al. by the reaction of lithium diisopropyl amide on tetraphenylphosphonium bromide as reported in J. Organo-metallic Chem., Vol. 110, pp. 49–57 (1976). The tetraarylphosphonium bromide compounds used as precursors are prepared by the palladium catalyzed reaction of the appropriate triarylphosphine with the corresponding bromoaryl compound.

The various embodiments of the present invention are further illustrated by the following examples. Examples 1–3 describe the preparation of the novel phosphine ligands and Example 4–11 describe the operation of the hydroformylation process of our invention.

EXAMPLE 1

The apparatus employed comprised a 500 mL, three-necked flask equipped with a reflux condenser, bare steel magnetic stirrer, pressure equalizing addition funnel and argon atmosphere. The flask was charged with 9-phenyldibenzophosphole (5.20 grams, 20 mmole; Strem chemical Co.) and 75 mL of dry distilled tetrahydrofuran (THF). Lithium metal as wire was cleaned of its protective mineral oil and sliced in 0.03 gram pieces. Lithium (0.28 grams, 40 mmole) was added to the flask containing the solution of the organophosphorus compound This mixture was stirred at room temperature and the lithium dissolved after five hours leaving a dark yellow brown solution of the dibenzophospholyl anion and phenyl lithium. Dry THF (5 mL) and tert-butyl chloride (1.85 grams, 20 mmole) were charged to the addition funnel and added over 30 minutes to the lithio solution at room temperature and allowed to stir overnight at room temperature to selectively quench out the phenyllithium anion.

2,2'-Bis(bromomethy1)-1,1'-biphenyl (3.40 grams, 10 mmole) was added to the addition funnel and dissolved in 10 mL of dry THF. The dibromo compound may be obtained by the free radical catalyzed halogenation of 2,2'-bi-tolyl. The flask containing the dibenzophospholyl anion is chilled with a water-ice bath. The mixture was stirred vigorously as the dibromo compound was added dropwise to the chilled solution over 30 minutes. The solution color lightened by the end of the addition. The resulting mixture was allowed to stir at room temperature for an additional five hours. Methanol (5 mL) was added to quench out any remaining anion and resulted in a pale yellow mixture.

The THF and methanol were removed from the crude product by a nitrogen sweep on a steam bath. Nitrogen-purged water (100 mL) and toluene (100 mL) were added to the crude oil and the mixture was transferred to a separatory funnel under nitrogen. The water layer was drained and discarded and the organic layer was then washed twice with 50 mL of water to remove remaining salts. The toluene layer was isolated and the toluene removed by a nitrogen sweep on a steam bath. The yellow-orange oil was purified by crystallization from hexane/isopropanol solvent and washed with isopropanol. After drying, 3.05 grams of white crystalline product with a melting point of 154°-156° C. was isolated. The phosphorus 31 NMR absorption relative to 85% aqueous phosphoric acid was −11.94 PPM. The proton NMR absorptions relative to tetramethylsilane are: Complex overlapping multiplets aromatic ring protons 7.86 PPM−7.07 PPM, 16H; double-doublet centered at 2.82 PPM, 4H benzylic protons. The phosphine ligand thus prepared has the structure:

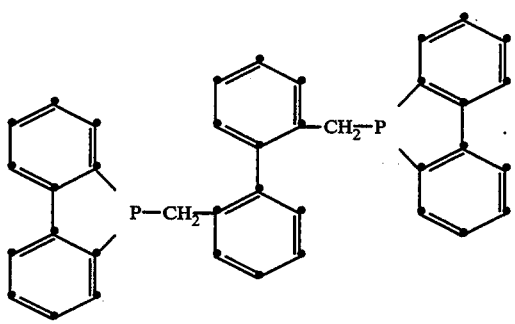

EXAMPLE 2

The apparatus employed comprised a 1-liter, three-necked flask equipped with a mechanical stirrer, reflux condenser, pressure equalizing addition funnel, thermometer, heating mantle and nitrogen atmosphere. The flask was charged with magnesium metal chips (4.86 grams, 0.20 mole) and dry distilled THF (150 mL). The addition funnel was charged with dry THF (50 mL) and 2-bromo-4-tert-butyltoluene (45.43 grams, 0.20 mole). The Grignard reaction was initiated by the addition of 5 mL of the solution and heating to reflux. The rest of the bromo compound was added at reflux over one hour and then stirred at reflux an extra hour to drive the reaction to completion. This Grignard reagent was transferred to a 250 mL pressure equalizing addition funnel under nitrogen for the next part of the synthesis.

A second 1-liter, three-necked flask was set up with a reflux condenser, nitrogen atmosphere, football shaped magnetic stirrer, heating mantle and pressure equalizing addition funnel. This flask was charged with anhydrous NiBr2 (0.44 grams, 0.002 mole), triphenylphosphine (5.24 grams, 0.02 mole) and dry, nitrogen-purged toluene (200 mL). A second charge of 2-bromo-4-tert-butyltoluene (45.43 grams, 0.20 mole) was added to the flask containing the Ni and this was heated to reflux. The 250 mL, pressure-equalizing addition funnel containing the Grignard reagent was placed in position on the flask containing the Ni and second charge of bromo compound. The Grignard reagent was added to the stirred flask over two hours at reflux where the mixture darkened to a dark homogeneous brown color. The mixture was stirred an extra 16 hours at gentle reflux to drive the reaction to completion.

The reaction was worked up by quenching the crude brown mixture with 200 mL of 5 percent aqueous ammonium chloride with the addition of 3 mL of 30 percent hydrogen peroxide to destroy the residual Ni complexes. After stirring and settling, clean separation occurred yielding a pale blue-green aqueous layer and light yellow organic layer with no emulsion interface. The layers were separated and the aqueous layer discarded. The resulting organic layer was washed with 400 and 200 mL portions of water. The organic layer was then distilled, first at atmospheric pressure to remove the low-boiling solvents and then at 3 torr on a simple distillation apparatus. A forerun collected at 80°-130° C. contained mostly starting bromo compound and tert-butyltoluene (net weight 1.37 grams). The product, 5,5'-di-tert-butyl-2,2'-bitolyl, distilled at 175°-180° C. (net weight 46.98 grams). The proton NMR absorptions relative to tetramethylsilane are: overlapping multiplets, 7.10-7.32 PPM, 6H ring aromatic protons; singlet, 2.03 PPM, 6H methyl; singlet, 1.32 PPM, 18H tert-butyl.

This part of the ligand synthesis was carried out in an apparatus comprised of a 200 mL, three-necked flask equipped with a magnetic stir bar, glycol chilled reflux condenser, pressure equalizing addition funnel, nitrogen sweep across the top of the reflux condenser that will remove hydrobromic acid vapor by-product, hot-plate stirrer and 500 watt "sun lamp". The flask was charged with 5,5'-di-tert-butyl-2,2'-bitolyl (14.73 grams, 50 mmole) and dichloromethane (90 mL). The mixture in the flask was heated to reflux and the lamp was then turned on, illuminating the flask. Bromine (15.98 grams, 5.12 mL, 100 mmole) was added to the mixture from the addition funnel over a two-hour period. The decolorization of bromine in the flask was rapid. The lamp was kept on an additional three minutes following the completion of the addition to consume the residual bromine vapor in the flask. The crude product solution was stripped of the dichloromethane with nitrogen leaving a glassy solid. This was treated with dichloromethane (10 mL) and hexane (90 mL) to induce crystallization of the product, 2,2'-di(bromomethyl)-5,5'-di-tert-butyl-1,1'-biphenyl. A total of three crops of the desired product was isolated by hexane crystallization to give 10.25 grams of white crystals. Melting point 124°-125° C. Proton NMR absorptions relative to tetramethylsilane: complex multiplet 7.46-7.26 PPM, aromatic ring protons; double-doublet centered at 4.26 PPM, benzylic protons; singlet 1.35 PPM tert-butyl protons.

The apparatus employed was the same as that used in Example 1. Clean lithium metal cut in 0.03 gram pieces (0.28 grams, 40 mmole) was added to the flask containing a solution of 9-phenyldibenzophosphole (5.20 grams, 20 mmole) in dry THF (50 mL). The resulting mixture was stirred a total of 4 hours at room temperature to form a brown colored solution of the lithio species. THF (10 mL) and tert-butyl chloride (1.85 grams, 20 mmole) were added dropwise from the addition funnel to the lithio solution at room temperature over 30 minutes and the resulting mixture was warmed to 45° C. and held at that temperature for an additional 30 minutes. The lithio dibenzophosphole anion solution was chilled with a water-ice bath. A solution of 5,5'-ditert-butyl-2,2'-di(bromomethyl)-1,1'-biphenyl (4.52 grams, 10 mmole) in 50 mL of THF was added from the pressure equalizing addition funnel to the anion mixture with stirring over 30 minutes and the mixture was stirred at room temperature overnight.

The crude mixture was quenched with 300 mL of nitrogen-purged water and 100 mL of hexane. The two-phase mixture was transferred to a separatory funnel with a nitrogen atmosphere and the water layer was separated and discarded. The organic layer was washed with two portions of nitrogen-purged water. The hexane solvent was removed by a nitrogen sweep on a steam bath leaving the crude product as an oil. The crude product was purified by column chromatography on a 25.4 cm by 19 mm (10 inch by 0.75 inch) diameter column of neutral alumina using toluene/hexane (⅓) to elute the desired product. The product was isolated and crystallized from hexane to give 3.22 grams of crystalline product having a melting point of 193°–198° C. and the structure:

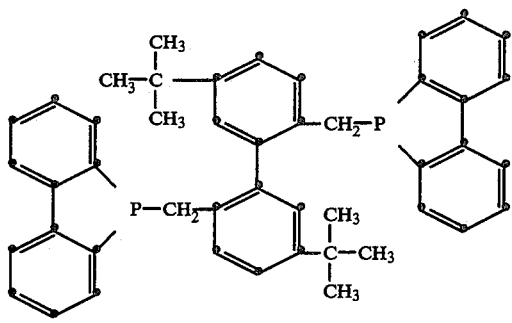

The phosphorus 31 NMR absorption relative to 85% aqueous phosphoric acid was −14.75 PPM. The proton NMR absorptions relative to tetramethylsilane are: overlapping multiplets 7.84–7.10 PPM, aromatic ring protons; doublet centered at 2.56 PPM, benzylic protons; singlet 1.36 PPM, tert-butyl protons.

EXAMPLE 3

The apparatus employed comprised a 250 mL, round-bottomed flask equipped with a reflux condenser, a nitrogen atmosphere and a football-shaped magnetic stirrer. The flask was charged with tri(4-tert-butylphenyl)phosphine (9.02 grams, 20.98 mmole), bis(benzonitrile) palladium(II) dichloride catalyst (77 mg, 0.20 mmole), 4-bromo-tert-butylbenzene (8.52 grams, 40 mmole) and tert-butylbenzene (100 mL). The tri(4-tert-butylphenyl)phosphine was made by the reaction of the 4-bromomagnesium tert-butylbenzene with phosphorus trichloride by a standard method. This mixture was heated at reflux for 72 hours and then cooled. The insoluble quaternary phosphonium product, tetra(4-tert-butylphenyl)phosphonium bromide, was filtered in an inert atmosphere by suction, washed with toluene and dried to obtain 8.66 grams of white crystals having a melting point greater than 320° C. The phosphorus 31 absorption of this material relative to 85% aqueous phosphoric acid was 20.41 PPM. The proton NMR absorptions relative to tetramethylsilane are: symmetrical multiplet 7.76–7.52 PPM, aromatic ring protons; 1.38 PPM, tert-butyl protons.

The apparatus employed in this part of the synthesis comprised a 250 mL, three-necked flask equipped with a magnetic stirrer, reflux condenser, nitrogen atmosphere, pressure equalizing addition funnel and a hot plate stirrer. The flask was charged with tetra(4-tert-butylphenyl)phosphonium bromide (6.43 grams, 10 mmole) and lithium diisopropyl amide (3.21 grams, 30 mmole). Dry distilled THF (50 mL) was added dropwise from the addition funnel to the two solids in the flask at room temperature. The mixture then was heated to reflux as the solids dissolved leaving a dark red-brown solution. After refluxing for 20 hours, the color of the mixture had not changed. After cooling to room temperature, the mixture was quenched with 15 mL of methanol resulting in a brown solution which was added under nitrogen to a separatory funnel containing 600 mL of water and 100 mL of dichloromethane and shaken. The dichloromethane layer was drained and collected under nitrogen. The aqueous layer was reextracted twice with 50 mL portions of dichloromethane. The combined dichloromethane layers were washed with 500 mL of water and the dichloromethane solvent was removed by sweeping with nitrogen, leaving a crude brown crystalline solid. This crude solid was purified by passing through a 15.2 by 1.9 cm (6 inch by 0.75 inch) diameter neutral alumina column with a 1:1 v/v mixture of hexane/toluene solvent under nitrogen. The solvent was removed by a nitrogen sweep and vacuum leaving 3.42 grams of white crystals. This material was recrystallized from 50 mL of a 3:1 v/v mixture of isopropanol/toluene solvent and dried to yield 1.2 grams of analytically pure 9-(p-tert-butylphenyl)-3,6-di-tert-butyldibenzophosphole having a melting point of 226°–229° C. The phosphorus 31 NMR absorption of this material relative to phosphoric acid was −14.41 PPM. The proton NMR absorption spectra relative to tetramethylsilane was: singlet 7.96 PPM, 2H 2-position ring protons; double-doublet 7.61 PPM, 2H meta-ring protons of 9-phenyl group; double-doublet 7.38 PPM, 2H ortho-ring protons of 9-phenyl group; singlet 7.26 PPM, 2H 4-position ring protons; singlet 7.24 PPM, 2H 2-position ring protons; singlet 1.39 PPM, 18H tert-butyl protons; singlet 1.24 PPM, 9H tert-butyl protons.

The apparatus employed in the final step of the phosphine ligand preparation comprised a 100 mL, three-necked flask equipped with an argon atmosphere, a bare steel magnetic stirrer, reflux condenser, pressure equalizing addition funnel and hot plate stirrer. The flask was charged with 9-(p-tert-butylphenyl)-3,6-di-tert-butyl-dibenzophosphole (1.13 grams, 2.63 mmole) and dry THF (15 mL). Lithium metal was cleaned and cut into 0.01 gram pieces and weighed on the analytical balance to within 1 mg of the 39 mg (5.61 mmole) charge. This lithium metal was added at room temperature and allowed to stir at room temperature for 5 hours at which time all lithium had dissolved leaving a clear brown solution of the lithium anions. The flask containing the anion was warmed to approximately 40° C. and tert-butyl chloride (0.26 grams, 2.79 mmole) in THF (5 mL) was added by means of the addition funnel to the stirred mixture over 20 minutes to consume the t-butylphenyl lithium. The resulting mixture was stirred an extra 30 minutes to complete the reaction. The color at the end was clear orange. The flask containing the anion was chilled with water-ice and a solution of 2,2'-di(-bromomethyl)-1,1'-biphenyl (0,475 grams, 1.39 mmole) in THF (10 mL) was added dropwise from the addition funnel to the cold solution with stirring until the orange color of the anion just disappeared. This required the addition of 80 percent of the dibromo compound. This was stirred at room temperature overnight.

The crude product solution was added under nitrogen to a separatory funnel containing 100 mL of water and 50 mL of dichloromethane. An emulsion was encountered that was broken by the addition of 10 mL of saturated ammonium chloride solution. The dichloromethane layer was collected under nitrogen and the aqueous layer was re-extracted with another 50 mL of dichloromethane. The combined extracts were then washed with 200 mL of nitrogen-purged water. The organic layer was stripped with nitrogen and subjected to heating at 0.5 tort to obtain 1.15 grams of the product as a glassy brittle solid. The phosphorus 31 absorption relative to phosphoric acid was −16.76 PPM. The proton NMR absorption spectrum relative to tetramethylsilane was: complex overlapping multiplets 7.86–7.08 PPM, aromatic ring protons; double-doublet centered at 2.76 PPM, benzylic protons; doublet 1.37 PPM, tert-butyl protons. The product has the structure:

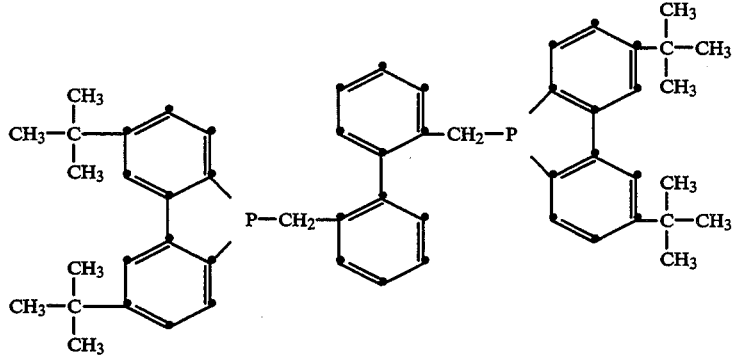

The following examples illustrate the hydroformylation of olefins in accordance with the present invention. The reactor is a vertically arranged stainless steel pipe having a 2.5 cm inside diameter and a length of 1.2 meters. The reactor has a filter element welded into the side down near the bottom of the reactor for the inlet of gaseous reactants. The reactor contains a thermowell which is arranged axially with the reactor in its center for accurate measurement of the temperature of the hydroformylation reaction mixture. The bottom of the reactor has a high pressure tubing connection that is connected to a cross. One of the connections to the cross permits the addition of non-gaseous reactants such as octene-1 or make-up solvent, another leads to the high-pressure connection of a differential pressure (D/P) cell that is used to measure catalyst level in the reactor and the bottom connection is used for draining the catalyst solution at the end of the run.

When used for the hydroformylation of propylene, the reactor is operated in a vapor take-off mode of operation. In this mode, the hydroformylation reaction mixture or solution containing the catalyst is sparged under pressure with the incoming reactants of propylene, hydrogen and carbon monoxide as well as any inert feed such as nitrogen. As butyraldehyde is formed in the catalyst solution it and unreacted reactant gases are removed as a vapor from the top of the reactor by a side-port. The vapor removed is chilled in a high pressure separator where the butyraldehyde product is condensed along with some of the unreacted propylene. The uncondensed gases are let down to atmospheric pressure via the pressure control valve. These gases pass through a series of three dry-ice traps where any other aldehyde product is collected. The product from the high pressure separator is combined with that of the traps, and is subsequently weighed and analyzed by standard gas/liquid phase chromatography (GLC) techniques for the net weight and normal/iso ratio of the butyraldehyde product.

The gaseous feeds to the reactor are fed to the reactor via twin cylinder manifolds and high pressure regulators. The hydrogen passes through a commercially available "Deoxo" (registered trademark of Engelhard Inc.) catalyst bed to remove any oxygen contamination and through a flow controller D/P cell and control valve. The carbon monoxide passes through a similar "Deoxo" bed heated to 125° C., an iron carbonyl removal bed (as disclosed in U.S. Pat. No. 4,608,239), a flow controller D/P cell and control valve. Alternately, carbon monoxide flow can be controlled using a rotameter with a needle valve when low flows are required. Normally the nitrogen, which is used as an inert feed, is fed to the reactor via the rotameter. Propylene is fed to the reactor from feed tanks that are pressurized with hydrogen and is controlled using an armored rotameter in combination with a needle control valve. Propylene feed rate is measured by the rate of level drop in the tank in conjunction with the rotameter control point. All gases and propylene are passed through a preheater to insure vaporization of the liquid propylene leaving the armored rotameter. Any higher boiling liquid olefin feeds such as octene-1 are pumped into the reactor from the bottom cross using a small positive displacement feed pump. The amount of olefin fed in this manner is also measured by a small feed tank.

EXAMPLE 4

A catalyst solution consisting of 60 mgs of rhodium charged as a Rh(II)2-ethylhexanoate salt (0,583 mmole), 0.64 grams (1,166 mmole) of the phosphine ligand of Example 1 and 190 mL of 2,2,4-trimethyl-1,3-pentanediol monoisobutyrate solvent was prepared under nitrogen and was charged to the reactor under an argon blanket and the reactor top plug then was screwed in place. The reactor was pressured to 19 bars-absolute (260 psig) with hydrogen, carbon monoxide and nitrogen and heated to 125° C. Propylene feed was then started and the flows were adjusted to the following values which are reported as liters/minute at standard temperature and pressure (STP): hydrogen=4.31; carbon monoxide=2.00; nitrogen=0.96; and propylene=2.88. This is equivalent to having the following partial pressures in the feed to the reactor reported as bars absolute (psia): hydrogen=8 (116); carbon monoxide=3.72 (54); nitrogen=1.86 (27); and propylene=5.38 (78).

The hydroformylation reaction was carried out under the above flows for five hours. The butyraldehyde production rate for the last three hours of operation averaged 131.7 grams/hour for a catalyst activity of 2.2 kilograms butyraldehyde/gram of rhodium-hour. The product N:Iso ratio was 40.8/1.

EXAMPLE 5

This example illustrates the hydroformylation of propylene at 105° C. using a carbon monoxide partial pressure of 1.4 bars absolute (20 psia). The catalyst solution used in Example 4 was used in this example. The hydroformylation was carried out at 105° C. and the flows to the reactor were adjusted to the following values reported as liters/minute STP: hydrogen=4.31; carbon monoxide=0.75; nitrogen=2.21; and propylene=2.88. This corresponds to the following partial pressures in the feed, reported as bars absolute (psia): hydrogen=8 (116); carbon monoxide=1.38 (20); nitrogen=4.14 (60); and propylene=5.38 (78). The general operating procedure of Example 1 was repeated with a total reaction time of five hours at the target conditions. The average butyraldehyde production rate for the last three hours was 42.2 grams per hour with a N:Iso ratio of 64/1. This corresponds to a catalyst activity of 0.7 kilograms butyraldehyde/gram of rhodium-hour.

EXAMPLE 6

This example illustrates the hydroformylation of propylene at 105° C. using a carbon monoxide partial pressure of 2.76 bars absolute (40 psia). A catalyst solution consisting of 25 mg of Rh charged as the Rh(II)2-ethylhexanoate salt (0,243 mmole), the phosphine ligand of Example 1 (0.66 grams, 1.215 mmole) and 2,2,4-trimethyl-1,3-pentanediol monoisobutyrate solvent (190 mL) was prepared and charged to the reactor under argon and sealed with the reactor plug. The unit was brought to the following reactor conditions: Reactor temperature=105° C.; the flows, reported as liter/minute STP, to the reactor were: hydrogen=4.31, carbon monoxide=1.44, nitrogen=0.96 and propylene=2.88. These flow rates result in the following reactant partial pressures, reported as bars absolute (psia), in the feed: hydrogen=8.34 (121), carbon monoxide=2.76 (40), nitrogen=1.86 (27) and propylene=6 (87). The reaction produced butyraldehyde product at 8.0 grams per hour with a N:Iso ratio of 45/1. The corresponding catalyst activity was 0.5 kilograms butyraldehyde/gram of rhodium-hour.

EXAMPLE 7

A catalyst solution consisting of 33.45 mg of rhodium charged as Rh(II)2-ethylhexanoate (0.3251 mmole), 0.36 grams of the phosphine ligand of Example 1 (0.6502 mmole) and 100 mL of 2,24-trimethyl-1,3pentanediol monoisobutyrate solvent was prepared under nitrogen and charged to the reactor under an argon blanket and the reactor plug screwed in place. The reactor was pressured to 18.9 bars absolute (260 psig) with hydrogen, carbon monoxide and nitrogen and heated to 105° C. The reactor feed flows were adjusted to the following flows reported as liters/minute STP: hydrogen=1.46; carbon monoxide=1.58; and nitrogen=2.28 l/min. Octene-1 (100 mL, 71.5 grams) was pumped into the reactor over two hours. These flow rates result in the following reactant partial pressures, reported as bars absolute (psia), in the feed: hydrogen=5.17 (75); carbon monoxide=5.66 (82); and nitrogen=8.14 (118). The reactor temperature and the above flows were maintained for an additional two hours.

The contents of the reactor and the material collected in the high pressure separator were both analyzed by standard GLC techniques on a capillary GC. A total of 40.4 grams of nonanal was recovered as determined by the GLC analysis with a linear:branched product ratio of 55.3/1.

EXAMPLE 8

A catalyst solution consisting of 33.45 mg of Rh charged as Rh(II)2-ethylhexanoate (0.3251 mmole), 0.36 grams of the phosphine ligand of Example 1 (0.6502 mmole) and 150 mL of purified p-diisopropylbenzene solvent was prepared under nitrogen and was charged to the reactor under an argon blanket and then the reactor plug was screwed shut. The p-diisopropylbenzene solvent was purified by passing it through a short bed of neutral alumina under nitrogen in order to remove any peroxides present. The reactor was pressured to 18.9 bars absolute (260 psig) with hydrogen, carbon monoxide and nitrogen and heated to 105° C. The gaseous feed rates were adjusted to the following flow rates, reported as 1/min STP: hydrogen=1.46; carbon monoxide=0.81; and nitrogen=3.05. This is equivalent to having the following partial pressures in the feed, reported as bars absolute (psia): hydrogen=5.17 (75), carbon monoxide=2.9 (42), nitrogen=10.9 (158).

1,7-Octadiene was purified using the same method as with the solvent prior to use to remove any residual peroxide. This octadiene (50 mL, 37.3 grams) was pumped into the reactor over two hours at the above reactor conditions. The reactor conditions were continued for an additional two hours prior to shutting down. The contents of the reactor and the material collected in the high pressure separator were both analyzed using standard GLC techniques on a capillary instrument. A total of 12.6 grams of isomeric decanedialdehyde with a total linear:branched ratio of 28:1 was recovered. Additionally 8.2 grams of isomeric nonenaldehyde products were recovered.

EXAMPLE 9

A catalyst solution consisting of 60 mgs of Rh charged as Rh(II)2-ethylhexanoate salt (0,583 mmole), 0.77 grams of the phosphine ligand of Example 2 (1.166 mmole) and 190 mL of 2,2,4-trimethyl-1,3-pentanediol monoisobutyrate solvent was prepared under nitrogen and was charged to the reactor in the manner described above. The reactor was pressured to 18.9 bars absolute (260 psig) with hydrogen, carbon monoxide and nitrogen and heated to 105° C. Propylene feed was started and the flows to the reactor were adjusted to the following values, reported as liter/minute STP: hydrogen=4.31; carbon monoxide=0.81; nitrogen=0.96; and propylene=2.88. These flows correspond to the following partial pressures, reported as bars absolute (psia) in the feed to the reactor: hydrogen=9.1 (132); carbon monoxide=1.72 (25); nitrogen=2 (29); and propylene=6.07 (88). These conditions were maintained for five hours. The average yield of butyraldehyde product was 40.6 grams per hour for the last three hours for a catalyst activity of 0.67 kilogram butyraldehyde/gram of rhodium-hour with the average N:Iso ratio of the product being 179:1.

EXAMPLE 10

The procedure of Example 9 was repeated except that the reactor temperature was increased to 110° C. The reactor conditions were maintained for five hours and the average butyraldehyde production from the last 3 hours was used for the data. Butyraldehyde production averaged 95.9 grams per hour with a product N:Iso ratio of 288:1. The catalyst activity was 1.2 kilograms butyraldehyde/gram of rhodium-hour.

EXAMPLE 11

A catalyst solution consisting of 40 mgs of Rh charged as the Rh(II)2-ethylhexanoate salt (0.3887 mmole), 0.60 grams of the phosphine ligand of Example 3 (0.7775 mmole) and 190 mL of 2,2,4-trimethyl-1,3-pentanediol monoisobutyrate solvent was prepared under nitrogen and charged to the reactor in the manner described above. The reactor was pressured to 260 psig with hydrogen, carbon monoxide and nitrogen and heated to 105° C. Propylene feed was then started. The following flow rates, reported as liter/minute STP, were fed to the reactor for about two hours before equipment failure terminated the run: hydrogen=4.31; carbon monoxide=0.76; nitrogen=0.96; and propylene=2.88. These flows correspond to the following partial pressures, reported as bars absolute (psia), in the feed to the reactor: hydrogen=9.17 (133); carbon monoxide=1.59 (23); nitrogen=2.07 (30); and propylene=6.14 (89). The reaction produced 65 grams of butyraldehyde with a N:Iso ratio of 38:1. The catalyst activity during this period was equivalent to 1.63 kilograms butyraldehyde/gram of rhodium-hour.

The invention has been described in detail with particular reference to preferred embodiments thereof, but it will be understood that variations and modifications will be effected within the spirit and scope of the invention.

We claim:

1. A process for preparing an aldehyde which comprises contacting an olefin, hydrogen and carbon monoxide with a solution of a catalyst system comprising rhodium and a phosphine compound having the general formula

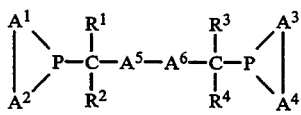

wherein:
each of $A^1$, $A^2$, $A^3$ and $A^4$ is an arylene radical wherein (i) each phosphorus atom P is bonded to a ring carbon atom of $A^1$ and $A^2$ and to a ring carbon atom of $A^3$ and $A^4$, (ii) $A^1$ and $A^2$, and $A^3$ and $A^4$ are bonded to each other by ring carbon atoms and (iii) each of the residues

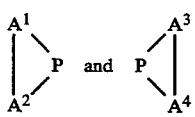

constitutes a 5-membered ring;
each of $A^5$ and $A^6$ is an arylene radical wherein $A^5$ and $A^6$ are bonded to each other and to residues $R^1$—C—$R^2$ and $R^3$—C—$R^4$ by ring carbon atoms and $R^1$—C—$R^2$ and $R^3$—C—$R^4$ are connected to each other through a chain of 4 carbon atoms; and $R^1$, $R^2$, $R^3$ and $R^4$ each represents hydrogen or a hydrocarbyl radical containing up to about 8 carbon atoms; and wherein the mole ratio of (1):(2) is at least 1:1.

2. Process according to claim 1 wherein the concentration of rhodium in the solution is in the range of about 50 to 300 mg per liter and the process is carried out at a temperature of about 50° to 135° C. at a pressure in the range of ambient to about 36 bars absolute.

3. Process according to claim 1 wherein the concentration of rhodium in the solution is in the range of about 50 to 300 mg per liter; the process is carried out at a temperature of about 50° to 135° C. at a pressure in the range of ambient to about 36 bars absolute; and in the phosphine compounds the arylene groups represented by each of $A^1$, $A^2$, $A^3$, $A^4$, $A^5$ and $A^6$ are selected from the divalent radicals having the formulas:

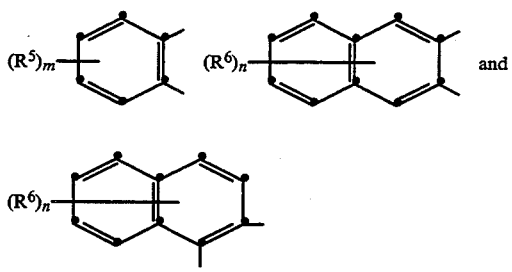

wherein $R^5$ and $R^6$ are independently selected from alkyl, alkoxy, hydroxy, halogen, formyl, alkanoyl, aroyl, carboxyl, carboxylate salts, alkoxycarbonyl, alkanoyloxy, cyano, sulfonic acid and sulfonate salts;
m is 0 to 4; and
n is 0 to 6.

4. Process according to claim 1 wherein the olefin is a mono-α-olefin of 2 to 10 carbon atoms.

5. Process according to claim 3 wherein the olefin is a mono-α-olefin of 2 to 10 carbon atoms.

6. A process for preparing an aldehyde which comprises contacting an olefin, hydrogen and carbon monoxide at a temperature of about 50° to 135° C. at a pressure in the range of ambient to about 36 bars absolute with a solution of a catalyst system comprising rhodium and a phosphine compound having the general formula

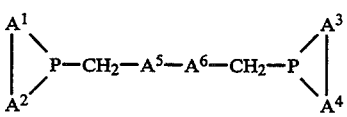

wherein:
each of $A^1$, $A^2$, $A^3$ and $A^4$ is an arylene radical wherein (i) each phosphorus atom P is bonded to a ring carbon atom of $A^1$ and $A^2$ and to a ring carbon atom of $A^3$ and $A^4$, (ii) $A^1$ and $A^2$, and $A^3$ and $A^4$ are bonded to each other by ring carbon atoms and (iii) each of the residues

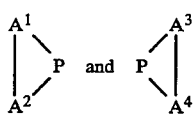

constitutes a 5-membered ring;

each of $A^5$ and $A^6$ is an arylene radical wherein $A^5$ and $A^6$ are bonded to each other and to each of methylene groups $CH_2$ by ring carbon atoms and methylene groups $CH_2$ are connected to each other through a chain of 4 carbon atoms; and the arylene groups which each of $A^1$, $A^2$, $A^3$, $A^4$, $A^5$ and $A^6$ represent are selected from the groups having the formulas

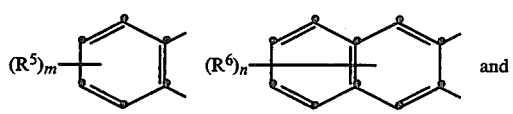

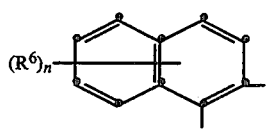

wherein $R^5$ and $R^6$ are independently selected from alkyl of up to about 4 carbon atoms; and m and n independently are 0, 1 or 2; and wherein the concentration of rhodium in the solution is in the range of about 50 to 300 mg per liter.

7. A process according to claim 6 wherein the olefin is a mono-α-olefin of 2 to 10 carbon atoms; and the phosphine compound has the general formula

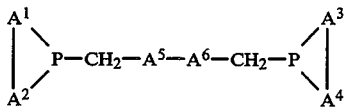

wherein:

each of $A^1$, $A^2$, $A^3$ and $A^4$ is an arylene radical wherein (i) each phosphorus atom P is bonded to a ring carbon atom of $A^1$ and $A^2$ and to a ring carbon atom of $A^3$ and $A^4$, (ii) $A^1$ and $A^2$, and $A^3$ and $A^4$ are bonded to each other by ring carbon atoms and (iii) each of the residues

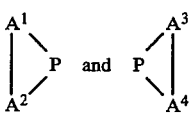

constitutes a 5-membered ring;

each of $A^5$ and $A^6$ is an arylene radical wherein $A^5$ and $A^6$ are bonded to each other and to each of methylene groups $CH_2$ by ring carbon atoms and methylene groups $CH_2$ are connected to each other through a chain of 4 carbon atoms; and the arylene groups which each of $A^1$, $A^2$, $A^3$, $A^4$, $A^5$ and $A^6$ represent are selected from the group having the formulas

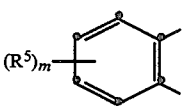

wherein each $R^5$ independently is selected from alkyl of up to about 4 carbon atoms; and m and n independently are 0 or 1.

* * * * *